United States Patent [19]

Morgan

[11] Patent Number: 4,654,307
[45] Date of Patent: Mar. 31, 1987

[54] NOVEL BACTERIA CONTAINING A PLASMID HAVING A TRNA CODE

[75] Inventor: Edward A. Morgan, Amherst, N.Y.

[73] Assignee: The Research Foundation of State University of New York, Albany, N.Y.

[21] Appl. No.: 467,438

[22] Filed: Feb. 17, 1983

[51] Int. Cl.[4] .................... C12N 1/20; C12N 15/00; C12N 1/00

[52] U.S. Cl. ................... 435/253; 435/172.3; 435/317; 935/29; 935/72; 935/73; 935/5

[58] Field of Search ............... 435/172.3, 317, 253, 435/849; 536/27; 935/3, 5, 29, 41, 73

[56] References Cited

U.S. PATENT DOCUMENTS 4,338,400 7/1982 Manis et al.
4,374,200 2/1983 Olsen .................................... 435/68

OTHER PUBLICATIONS

Morgan, E. et al., *J. Bact.* vol. 137, No. 1, pp. 507–516, 1979.
Keneriel, M. et al, *J. Bact.* vol. 132, No 3, pp. 931–949, 1977.
Nomura, M. et al, *Ann. Rev. Genet.* vol. 11, pp. 297–347, 1977.
Hallewell et al, *Gene* vol. 9, pp. 27–47, 1980.
Chakrabarty, A., *Genetic Engineering*, CRC Press, Inc., pp. 97–102, 1978.
Boros et al, *Nucleic Acids Research*, vol. 6, No. 5, 1979, pp. 1817–1830.
Morgan et al, *Cell*, vol. 13, pp. 335–344, 1978.
Clarke et al, *Cell*, vol. 9, pp. 91–99, 1976.
"Molecular Cloning a Laboratory Manual", Maniatis et al, 1982, Cold Spring Harbor Labor., pp. 100–101.
"Ribosomal RNA Genes in *Escherchia Coci*", Morgan, The Cell Nucleus, vol. X, 1982, pp. 1–29.
"Gene-Protein Index of *Escherichia Coli* K-12"; Niedhardt et al, *Microbiological Reviews*, Jun. 1983, pp. 231–284.

*Primary Examiner*—Thomas G. Wiseman
*Assistant Examiner*—Jayme A. Huleatt
*Attorney, Agent, or Firm*—Michael L. Dunn

[57] ABSTRACT

A bacterium which comprises chromosomal DNA which lacks a DNA sequence to code for a tRNA for an amino acid and which bacterium further comprises a plasmid which has a DNA sequence which does effectively code for said tRNA for said amino acid. The invention further includes such a bacterium wherein the DNA sequence for the tRNA for the amino acid is located in a ribosomal RNA operon preferably between a ribosomal RNA promoter and a ribosomal RNA promoter termination sequence within the plasmid.

4 Claims, 4 Drawing Figures

NOVEL BACTERIA CONTAINING A PLASMID HAVING A TRNA CODE

BACKGROUND ART

Historically, man has manipulated the genetic structure of microorganisms, plants and animals primarily by selection of desirable natural mutants of living organisms or by cross fertilization of organisms followed by selection of a desirable strain. Such methods have given us desirable microorganisms such as the yeasts that are used in baking and that are used in fermentation for the manufacture of beverages such as beer and wine. Other such microorganisms produce antibiotics and others are responsible for production of certain foods such as pickles and sauerkraut. Other selected microorganisms are used in desirable degradation processes such as the microorganisms used in waste disposal. Such genetic manipulation has not been limited to microorganisms and has also resulted in improved species of plants and animals such as hybrid food crops and animals having desirable meat, milk or egg production.

It has recently become technically possible to move genes from one cell type to another (usually from plants and animals to bacteria) by use of techniques developed in the study of molecular biology of prokaryotic cells (cells which are prenucleus) and eukaryotic cells (cells which contain a nucleus which are usually cells of higher organisms). Such a result is exceedingly desirable since man no longer has to rely on the appearance of spontaneous mutants. It is now possible to transfer genes from higher plants or animals (eukaryotic cells) to place them into bacterial cells (prokaryotic cells) by means of a vector. "Genes", as used herein, means a segment of DNA (deoxyribonucleic acid) which carries genetic information. "Vector", as used herein, is any composition or structure which can carry genes into the cell for replication (manufacture of additional similar DNA fragments), and also usually for transcription (manufacture of an RNA segment) and translation (manufacture of a polypeptide, usually a protein, from the information contained in an RNA segment). The vector is usually a phage virus to which the gene has been attached or a plasmid (circular rings of of DNA which are relatively small in size when compared with the length of chromosomal DNA). Chromosomal DNA is a long string of DNA which contains most of the genetic information in a cell.

The structure of DNA and RNA (ribonucleic acid) is based upon the arrangement of bases along alternating residues of certain sugars and phosphate. In the case of DNA, the alternating sugar residue is deoxyribose and in the case of RNA, the alternating sugar residue is ribose. The bases in the case of DNA are radicals of the chemicals thymine, cytosine, adenine, or guanine. In RNA, the bases are uracil, cytosine, adenine, or guanine. It is the arrangement of the bases which determines the genetic information. RNA is usually either messenger RNA (mRNA) which carries information from the DNA as an intermediary in the formation of polypeptides or is a transfer RNA (tRNA) which acts between the messenger RNA and amino acids to combine the amino acids in a particular sequence based upon the sequence and information contained in the messenger RNA. The transfer RNA seems to attach to both the information RNA and to a particular amino acid thus arranging the amino acids in the proper order. Each amino acid has its own transfer RNA which recognizes only particular sequence along a messenger RNA thus making certain that the old sequence in the messenger RNA is properly translated into the appropriate amino acid. Sequences of amino acids (polypeptides), usually a protein, may have many different functions depending upon the particular sequence. Such polypeptides may for example act as enzymes which are organic catalysts, hormones which act as regulators, antibodies which are produced in response and defense against foreign materials called antigens, structural and contractile proteins and blood and plasma proteins including albumins, fibrinogen vital in blood clotting and hemoglobin which carries oxygen.

It has been known that bacterial plasmids such as those found in the bacterial genuses salmonella, shigella, proteus, bacillus, pseudomonoas, streptomyces and all gram negative enteric bacteria such as *Escherichia coli* could be cleaved, new genetic codes (usually for a desired polypeptide) could be then inserted into the plasmid and the plasmid could then be replaced into a bacteria for replication generally followed by transcription and translation to form the desired polypeptide structure. "Cleaved", as used herein, is intended to mean cleaved or broken. "Restricted", is intended to mean cleaved by any means but usually by use of a restriction enzyme.

It has been further recognized that one method for cleaving is by utilizing restriction enzymes followed by insertion of the desired DNA sequence. In particular, such methods are set forth in "Molecular Cloning A Laboratory Manual" by Maniatis et al, published 1982 by Cold Spring Harbor Laboratory. Table 4.1 beginning on page 100 of the manual lists numerous restriction enzymes and the sequence and location of cleavage.

Although such procedures are well known to those skilled in the art, there remain serious problems with respect to the utilization of inserted plasmids for replication of the plasmid, transcription of the inserted sequence to form the appropriate RNA and translation of messenger RNA to the appropriate polypeptide.

In the prior art, it was recognized that methods had to be used to maintain the desired plasmid within the bacterial organism. One effective procedure was to include a gene for antibiotic resistance in the plasmid and then grow the bacteria in a media containing the particular antibiotic. The result was that only bacteria which contained the plasmid could continue to grow since bacteria without the plasmid were unable to cope with the hostile environment. Such a method, however, required that antibiotics be added to the growth medium, which in commercial production was an undesirable, costly and inconvenient step. Furthermore, there was a tendency of many microorganisms to develop the ability to resist antibiotics by a mutation on the chromosome which then made the plasmid unnecessary within the cell.

It was also known in the prior art that bacteria having a gene for an enzyme to make an essential protein, which gene was defective due to the presence of a nonsense codon, could function when a plasmid, having a gene for an abnormal tRNA which could read the nonsense codon and insert a suitable amino acid, was present in the cell. In the absence of the plasmid, the bacteria would die since the essential protein would no longer be produced.

This method was somewhat effective; however, there was a tendency for the mutated gene for the enzyme to revert back to a normal gene and there was also a tendency for the chromosomal DNA to develop its own code for a tRNA which could read the nonsense codon, both of which made the plasmid unnecessary to the cell.

In the prior art, it was recognized that ribosomal RNA operators were strong operators but there was extreme difficulty in making the operators function outside of their natural location. It has recently been found that an operon containing ribosomal RNA operators could be made to function provided that the parts of both the beginning and end of the operon was utilized, i.e. especially the promoter and promoter termination sequence. The "promoter termination sequence" is the termination sequence properly associated with termination of transcription commencing at the promoter. The promoter termination sequence is in general the sequence which is desired for termination of transcription commencing at the promoter rather than premature termination which may be caused by undesirable nonsense codons or premature, usually undesirable, sequences which act as terminators located between the promoter and the promoter termination sequence. The promoter termination sequence has also been termed the "transcription termination sequence".

A complete ribosomal RNA operon, including the natural sequence between the promoter and promoter termination sequence, was inserted in the prior art into a plasmid (see Morgan et al "Some rRNA Operons in *E. coli* have tRNA Genes at their Distal Ends". Cell, Volume 13, pages 335–344 1978). Such a plasmid had little utility since the plasmid was exceedingly large, i.e., about 27,000 base pairs long and had an exceedingly large number of base pairs in the ribosomal RNA operon including operators, promoter, promoter termination sequence, and intermediate sequence (the sequence between the ribosomal RNA promoter and promoter termination sequence). The entire operon had a size of about 5,800 base pairs.

The large size of the plasmid made it unsuitable for genetic engineering purposes since plasmids of such large size are generally rapidly lost from a bacterial cell and since plasmids of such large size replicate slowly. In addition, the long operon made cleavage of the intermediate sequence, followed by insertion of a new desired DNA sequence, impractical. Such impracticality partially results due to the large number of restriction nuclease sites in such a long intermediate sequence and in such a large plasmid. Furthermore, such sites and their location are difficult to characterize. In addition, the insertion of an additional sequence into such a large plasmid would make the plasmid even more unstable in the bacterial organism.

In the prior art, it was also recognized that RNA's could be analyzed by gel electrophoresis. C. Ikemura et al "Small Ribonucleic Acids of *Escherichia coli:* 1. Characterization by Polyacrylamide Gel Electrophoresis and Fingerprint Analysis", Journal of Biological Chemistry, Vol 248, pp. 5024–5032 and Peacock, et al "Resolution of Multiple Ribonucleic Acid Species by Polyacrylamide gel Electrophoresis" Biochemistry Vol 6, pp. 1818–1827. It was also recognized that certain tRNA's from plasmids could be analyzed by gel electrophoresis as discussed by Ikemura et al "Expression of Spacer tRNA genes in Ribosomal RNA Transcription Units carried by Hybrid ColE1 Plasmids in *E.coli*", Cell, Vol 11, pp. 779–793. Such test procedures, eg. for analyzing for transfer RNA's, had never been used in a small plasmid which rapidly replicates to test for transcription of a gene upstream of the transfer RNA sequence.

BRIEF DESCRIPTION OF THE INVENTION

In accordance with the present invention, a bacterium is provided which comprises chromosomal DNA which lacks a DNA sequence which effectively codes for a functional tRNA for at least one amino acid for which there is a known genetic code and which bacterium further comprises a plasmid which has a DNA sequence which does effectively code for said tRNA for said amino acid. The invention further includes such a bacterium wherein the DNA sequence for the tRNA for the amino acid is located in a ribosomal RNA operon preferably between a ribosomal RNA promoter and a ribosomal RNA promoter termination sequence within the plasmid. "Ribosomal RNA operon" as used herein is an operon containing a ribosomal RNA functional group. A "ribosomal RNA functional group" is a ribosomal RNA promoter, a ribosomal RNA promoter termination sequence, or a ribosomal RNA read through sequence. A read through sequence is a sequence which causes transcription of an intermediate DNA sequence through a sequence which normally would terminate more of the transcription of the intermediate sequence in the absence of the read through sequence.

In accordance with the invention, a plasmid is provided which contains a ribosomal RNA operon. The operon has fewer than 2,000 base pairs in a naturally occuring sequence. "Naturally occuring sequence" as used herein means that the sequence naturally occurs in ribosomal RNA operon. "Naturally sequentially occur" means to naturally occur in a ribosomal RNA operon. The operon is intended to include the operator, promoter, any intermediate sequence and the promoter termination sequence. The plasmid further includes a DNA sequence which codes for a tRNA located between the promoter and the termination sequence and most preferably upstream from and proximate the promoter termination sequence.

The plasmid desirably has at least one restriction nuclease site present between the ribosomal RNA promoter and the ribosomal RNA promoter termination sequence.

In accordance with the present invention methods for preparation of the bacteria, plasmids and operons of the invention are also provided.

The invention further includes a method for testing the replication, in a bacteria, of a particular sequence in a plasmid between a promoter and promoter termination sequence which comprises utilizing a plasmid having a DNA sequence for a tRNA also located between the promoter and the promoter termination sequence so that transcription of the particular sequence would also probably result in transcription of the tRNA and testing for the tRNA as an indicator of said transcription and probable translation.

DETAILED DESCRIPTION OF THE INVENTION

As previously discussed the bacteria of the present invention, which lack a DNA sequence which effectively codes for a functional tRNA for at least one amino acid for which there is a known genetic code and which further comprises a plasmid which does effectively code for said tRNA, are very useful. The bacteria permit genetic sequences within plasmids to stably remain within the bacteria after the plasmids are inserted. Furthermore, the plasmids are stable without the addition of antibiotics or other chemicals to the growth medium and there is little if any genetic reversion to a bacterial form which would make the plasmid unnecessary thus increasing the tendency for it to leave the cell. "Functional tRNA" means a tRNA which can effectively act as an intermediary between a messenger RNA sequence for a particular amino acid and the amino acid to align the amino acid for proper combination into an amino acid chain (polypeptide).

The tRNA for which there is no functional code on the chromosome and for which there is a functional code on the plasmid may be any tRNA for an amino acid necessary for growth of the bacteria. Such amino acids include glycine, alanine, valine, leucine, isoleucine, serine, cysteine, methionine, threonine, asparagine, glutamine, histidine, ariginine, lysine, phenylalanine, tyrosine, tryptophan, and proline. When the bacteria is E.coli, the preferred tRNA is for the amino acid tryptophan. This is true because the E.coli chromosome contains only one codon for tryptophan and it is thus easier to obtain a mutant wherein the sequence for tRNA for tryptophan (tRNA$^{trp}$) becomes deactivated.

In accordance with the present invention such bacteria are obtained by selecting a bacterium having a chromosomal tRNA sequence which is likely to mutate to a nonsense codom (one which is not recognized by any normal tRNA) and inserting an extra-chromosomal source for the tRNA. When a mutation occurs, the extra-chromosomal source for the tRNA becomes essential to the existance of the bacterium. Such an extra-chromosomal source is usually supplied by a plasmid and once the mutation occurs which inactivates the chromosomal code for the tRNA, the plasmid cannot leave the cell until another extra-chromosomal source for the appropriate tRNA is supplied. The mutations to deactivate the chromosomal tRNA gene can either be spontaneous or optionally can be forced, e.g. by radiation. Once a bacterium is found having the appropriate chromosomal mutation, essentially any plasmid can be inserted into the bacterium provided that it contains a gene for the proper tRNA. Bacteria having the appropriate mutation can be selected from the growth media by methods known to those skilled in the art.

Plasmids suitable for use in accordance with the present invention include those plasmids which contain a ribosomal RNA operon. Such operons in plasmids according to the present invention carry a gene for tRNA and are especially desirable because they carry a gene for tRNA$^{trp}$. Such an operon includes a bacterial ribosomal RNA promoter, an intermediate sequence, a bacterial ribosomal RNA termination sequence, a gene within the intermediate sequence for tRNA$^{trp}$ and usually an operator. The preferred plasmids in accordance with the present invention are those plasmids containing a ribosomal RNA operon which contains fewer than 2,000 base pairs in a naturally occuring sequence. Such operons are highly desirable since, exclusive of added desired sequences, they are small and thus easily managed.

Sub-sequences which do not naturally occur in ribosomal RNA operons which can be inserted into the intermediate sequence between the promoter and promoter termination sequence can be essentially any DNA sequence which can be transcribed in the bacteria. When a ribosomal RNA read through sequence is present, greater flexibility occurs since more of such sub-sequences can be transcribed.

Examples of such intermediate sequences are those which code for messenger RNA for structural proteins, contractile proteins, antibodies, enzymes, blood proteins including gamma globulins, albumins, fibrinogens and hemoglobin and for polypeptide hormones. Specific examples of such polypeptide hormones are insulin, human growth hormone and interferon. Other such hormones are ACTH, lteinizing hormones, secretin, gastrin, parathyroid hormone and various hormone releasing hormones. Examples of such enzymes are the digestive enzymes including pepsin, trypsine, chymotrypsin, elastase, carboxypeptidase, peptidase, amylase, maltase, lactase, sucrase, and lipases. Other such enzymes are those responsible for DNA replication, transcription to RNA and translation from RNA to polypeptides and those enzymes such as restriction enzymes responsible for breaking down or cleaving DNA or RNA. Many other such enzymes could be mentioned since enzymes control essentially all biological chemical functions including chemical synthesis and chemical breakdown.

As previously discussed, the ribosomal RNA promoter is a very strong promoter which increases the efficiency of replication and thus increases the efficiency of translation. The promoter can act to transcribe DNA sequences to the desirable RNA sequence such as transfer RNA (tRNA) or messenger RNA (mRNA). The strong promotion of transcription of DNA sequence to messenger RNA also tends to increase the efficiency of translation to the appropriate polypeptide chain from the messenger RNA.

The strength of ribosomal RNA promoters in systems which have little utility as easy genetic engineering tools has previously been demonstrated. See e.g., Kjeldgaard et al, "Regulation of Biosynthesis of Ribosomes, in Nomura, M., Tissieres, A., and Lengyel, P. (Eds.), Ribosomes", Cold Spring Harbor Laboratories, N.Y., pages 369–392.

In *E. coli* ribosomal RNA transcription units are known and are identified as rrnA through H from seven different bacterial chromosomal locations. None of such ribosomal RNA transcription units naturally occur on a plasmid (although such units are known to occur on an episome which is an extremely large plasmid-like ring approximately one-half the size of a chromosome). For a discussion of such ribosomal RNA genes (for transcription to ribosomal RNA's) see Morgan "Ribosomal RNA Genes in *Escherichia coli*" The Cell Nucleus, Volume X, copyright 1982 by Academic Press Inc. The preferred ribosomal promoter is an rrnC promoter. The preferred bacterium for utilizing the plasmids and DNA sequences in accordance with the present invention is *Escherichia coli*.

As previously discussed the invention further includes a method for testing for replication, in a bacteria, of a particular sequence in a plasmid between a promoter and promoter termination sequence which comprises utilizing a plasmid having a DNA sequence for a tRNA also located between the promoter and the promoter termination sequence so that transcription of the particular sequence would also probably result in transcription of the tRNA and testing for the tRNA as an indicator of said transcription and probable translation. Most desirably, the sequence for the tRNA is located after the particular sequence proximate the termination sequence. "Proximate" in this context usually means within about 100 base pairs. The method for testing for the tRNA is preferably by using a tRNA tagged with a radioactive isotope, isolating the tRNA by gel electrophoresis and counting the tRNA to determine the tRNA concentration. Such methods for testing for RNA, for different purposes, as previously mentioned, are known to those skilled in the art.

In accordance with one of the methods of the invention, a plasmid of the invention can be made by treating another small plasmid of the present invention, i.e. a plasmid containing a ribosomal RNA operon containing a DNA sequence for tRNA, with an appropriate restriction enzyme. The small plasmid should have at least one restriction nuclease site between the promoter and promoter termination sequence. After such treatment, the treated plasmid is combined with a desired DNA sequence for replication and transcription having ends suitable for combination with the restricted sites of the plasmid. The resulting plasmid is then introduced into host bacteria and the bacteria is grown in a suitable medium to produce or replicate the desired plasmid. Such procedures, once the original plasmid of the present invention is available, are well known to those skilled in the art and are for example, set forth in "Molecular Cloning A Laboratory Manual" by Maniatis et al, published by Cold Spring Harbor Laboratory, 1982.

Such a method for making a certain type of plasmid, in accordance with the present invention, comprises treating a particular plasmid with a restriction enzyme. The particular plasmid contains an operon comprising a bacterial ribosomal RNA promoter, a bacterial ribosomal RNA promoter termination sequence and an intermediate sequence between the promoter and the promoter termination sequence. The operon has a length of fewer than 2,000 base pairs and desirably fewer than 1,000 base pairs. The operon contains at least one restriction nuclease site between the promoter and the promoter termination sequence within the intermediate sequence and contains a sequence which codes for tRNA$^{trp}$. After treatment with the appropriate restriction enzyme, the treated plasmid is combined with a DNA sequence having ends suitable for combination with the restricted sites of the plasmid. The resulting plasmid is then introduced into a host bacteria and the bacteria is grown in a suitable medium to produce the desired plasmid. The same method may be used whether or not the starting particular plasmid contains intermediate sequences such as the read through sequence.

The invention further includes a method for making a plasmid of the present invention containing a ribosomal RNA promoter and a ribosomal RNA promoter termination sequence and a small intermediate sequence, including a gene for a tRNA, by treating a plasmid of the prior art. Such plasmids of the prior art were too large for easy use in genetic engineering and the intermediate sequence, between the promoter and promoter termination sequence, was too large for practical use for genetic engineering.

In accordance with the present invention, the method comprises treating such a large plasmid with a restriction enzyme, permitting the cleaved plasmids to recombine, introducing resulting plasmids into bacteria, growing colonies of the resulting bacteria, obtaining purified plasmids from such colonies, analyzing the plasmids, selecting the appropriate plasmid and introducing the appropriate plasmid into a host bacteria to replicate the desired plasmid. In the event that the selected plasmid is still too large for practical use, the procedure may be repeated by again treating with a restriction enzyme, followed by recombination, reintroduction, growing of the colonies and obtaining purified plasmids followed by analysis and selection. While the technology to practice the individual steps of the method were well known to those skilled in the art, e.g., as described in "Molecular Cloning A Laboratory Manual" (previously cited) and in "Advanced Bacterial Genetics" by Davis et al, published by Cold Spring Harbor Laboratory, 1980, the combination of steps and of their use upon the particular starting materials were not previously known and were not practiced.

A method for making a certain type of plasmid in accordance with this method is as follows:

(a) A plasmid containing a ribosomal RNA operon containing in excess of 2,000 base pairs and containing a ribosomal RNA promoter, a ribosomal RNA termination sequence and a gene for a desired tRNA, is treated with a restriction enzyme. The cleaved plasmids are then permitted to recombine. The recombined plasmids are then introduced into bacteria and colonies of the resulting bacteria are grown. Purified plasmids are then obtained from such colonies and are analyzed.

(b) Step (a) is repeated as necessary until the appropriate plasmid is found containing the desired ribosomal RNA operon which contains fewer than 2,000 base pairs; and (c) The appropriate plasmid is introduced into a host bacteria to reproduce the desired plasmid.

Plasmids of the invention containing an intermediate subsequence which does not naturally occur may similarly be made by first introducing a desired sequence into the prior art plasmid of a size which is impractical for common use.

In accordance with such a method, a desired sequence, which does not naturally occur, is combined with a transposon, the transposon is introduced into a vector such as a phage or another plasmid, and the desired vector is then selected and purified by methods known to those skilled in the art. The vector is then introduced into a bacteria containing a prior art plasmid of large size having a ribosomal RNA promoter, a ribosomal RNA promoter termination sequence and a code near the termination sequence for a tRNA. A bacteria containing the resulting plasmid comprising a ribosomal RNA promoter, a ribosomal RNA promoter termination sequence and an intermediate sequence is then selected and the plasmid is purified. If the selected plasmid is too large or contains more than the desired number of base pairs in a natural sequence in the ribosomal RNA operon, the plasmid is further treated with a restriction enzyme as previously described. Again, the technology to practice the individual steps of this method of the present invention are known; however, the combined steps and their use upon the particular starting materials are not known for the purpose of obtaining a plasmid or operon of the present invention.

Plasmids of the present invention can also be made by cloning an operon of the invention onto a plasmid which did not previously contain such an operon. This method will be further discussed in the Examples.

Operons of the present invention having fewer than 2,000 sequential base pairs in a naturally occuring sequence can be isolated by restricting a plasmid of the present invention having restriction nuclease sites on each side of said operon with an appropriate restriction enzyme and isolating the restricted operon in accordance with known procedures. Desirably such restriction sites are within about 50 base pairs of the ends of the operon.

Replicating the plasmid, transcribing the plasmid and associated desired sequences into the appropriate RNA's and translating messenger RNA's into polypeptides (including proteins) is simply accomplished by growing a bacterium containing a desired plasmid of the invention in a suitable medium. Such growth techniques are well known to those skilled in the art as are preparation techniques for removing and purifying desired plasmid, RNA and polypeptide products. The invention includes the method for production of RNA which contains its DNA code in a plasmid which comprises growing a bacteria containing a plasmid of the invention in a suitable medium. The invention also includes the method wherein the RNA is messenger RNA and the bacteria produce a polypeptide by translation of the messenger RNA.

In accordance with the present invention, a natural sequential length between a ribosomal RNA promoter and promoter termination sequence in the operon is substantially reduced which permits easy characterization of the reduced sequence and permits stable insertion of the plasmid into a bacterium. Furthermore, such reduction of the natural sequence length between the promoter and promoter termination sequence and reduction of a plasmid size permits formation of a stable plasmid with a relatively large insertion of a sequence which does not naturally occur between the promoter and terminator. In addition, the utilization of a ribosomal RNA promoter results in a very strong promotion of sequences intermediate the promoter and promoter termination sequence to the appropriate RNA and the presence of a code for a tRNA, when used in conjunction with a bacterium which lacks such a code on the chromosome, stabilizes the plasmid.

The following examples serve to illustrate and not limit the present invention. All recombinant DNA procedures were performed as described by Maniatis, et al "Molecular Cloning A Laboratory Manual" published by Cold Spring Harbor Laboratories, Cold Spring Harbor, New York, 1982, pp. 1-545. Most of the bacterial strains discussed in the examples are described in Table 1. Some intermediate strains in strain construction are described in the text. pLC22-36 is a large plasmid having about 27,000 base pairs with a ribosomal RNA operon including termination sequence of about 5,800 base pairs and is described by Morgan et al "Some rRNA Operons in E. coli have tRNA Genes at Their Distal Ends" Cell, Vol 13, pp. 335-344 1978.

EXAMPLE 1

Nonsense suppressor tRNAs were isolated by selection of suppression of the trp(amber) his(amber) mutations in strain EM4 or the trp(amber) mutation in strain EM322. trp(amber) is a mutation wherein a sequence which codes for an enzyme for the manufacture of the amino acid tryptophan contains a nonsense codon which prevents transcription of the sequence in the absence of the special tRNA which can insert an amino acid at the nonsense codon. The amber nonsense codon is the sequence UAG(uracil adenine, guanine). His(amber) is a mutation wherein a required enzyme for the manufacture of the amino acid histidine contains a nonsense codon which can only be read in the presence of a special tRNA which can insert an amino acid at the nonsense codon during translation. The bacterial strains EM4 and EM322 are characterized in Table 1. Mutants of strain EM322 that contain a nonsense suppressor were subsequently subjected to selection for cells that had no nonsense suppressor by plating on minimal media that contained 0.2% lactose, 0.2% galactose, 0.4% glycerol, 50 grams per milliliter tryptophane and 50 grams per milliliter isoleucine and valine. Plaque formation by T4 phages with amber nonsense codon or ocher nonsense codon (UAA) mutations in essential genes was used to confirm the presence or absence of nonsense suppressors in certain strains.

The first step in construction of tRNA$^{trp}$-SU7X strains (strains which are devoid of a gene for tRNA$^{trp}$ on the chromosome) was introduction of F14 episome (similar to a plasmid except extremely large in size, almost half the size of the chromosome and containing chromosomal type information), Into EM322, selecting gene Ilv$^+$. F14 carries the ilvA operon and has only a single tRNA gene (tRNA$^{trp}$) capable of mutation to a nonsense suppressor. Amber suppressing mutations were then isolated in this strain as described by Morgan et al "Deletion Analysis of the Expression of rRNA Genes and Associated tRNA Genes carried by a Transducing Bacteriophage", Journal of Bacteriology, Vol 137, pp. 507-516, 1979. Mating experiments demonstrated that 17 of 44 isolates had a nonsense suppressor on F14, indicating that many of the remaining strains probably had a tRNA$^{trp}$-Su7 mutation on the chromosome. Such a mutation means that there was an available code on the chromosome to manufacture a tRNA which could read through the amber nonsense codon to insert an appropriate amino acid.

The nonsense suppressor in 8 individual chromosomal supressor mutants was then activated by selection for survivors on medium containing lactose and galactose, and loss of the nonsense suppressors was confirmed by the Trp$^-$ phenotype and by inability of the resulting strains to plaque T4(amber) phages. At this point, the eight strains represented in principle a collection of two mutations in any of several tRNA genes, or a mutation, followed by a reversion, in any of several tRNA genes. Attempts to sort out these possibilities by use of standard genetic techniques were difficult because these strains are recA (devoid of an enzyme to permit recombination) and also do not grow the specialized transducing bacteriophage P1. Therefore, the stabilization of plasmids carrying a tRNA$^{trp}$ gene was tested, as only chromosomal mutations that inactivate the tRNA$^{trp}$ gene would strongly stabilize plasmids that code for tRN$^{trp}$. To test plasmid stabilization, pRS4 (a plasmid described in Example 2) was introduced into the 8 strains that contained a chromosomal nonsense suppressor inactivated by a second mutation, and F14 was then cured from all eight strains by growth in the presence of acridine orange.

To maximize the tendency to segregate pRS4, the mutually incompatible plasmid pCDS1 was then transformed into these cells. pCDS1 is a plasmid previously constructed from (plasmid pBR322 and contains genes for chloramphenicol and tetracycline resistance. After a period of growth in the presence of chloramphenicol and tetracycline, seven of the isolates retained pRS4 in greater than 99% of the cells (no loss detected) while the remaining eighth transformant and strain EM322/pRS4/pCDS1 lost pRS4 from more than 99% of the cells. Seven of these isolates therefore must have mutations in the chromosomal tRNA$^{trp}$ gene that inactivate it which stabilizes pRS4 in the bacteria since pRS4 provides the necessary functional tRNA$^{trp}$. One of these was analysed by control experiments which showed that pCDS-1 was rapidly lost during growth in the absence of tetracycline or chloramphenicol, and that pRS4 was rapidly lost after introduction of pRS1 as an alternative source of tRNA$^{trp}$. The mutation in the tRNA$^{trp}$ gene in this strain is designated trpT-Su7X, and results in production of tRNA$^{trp}$-Su7X.

Strains containing the tRNA$^{trp}$-Su7X gene on the chromosome must always have an extra-chromosomal source of tRNA$^{trp}$ to grow. Therefore, a newly constructed plasmid that expresses tRNA$^{trp}$ must replace the resident plasmid if the plasmid stabilization property of this strain is to be realized. In practice, this can be easily effected by transforming with the new plasmid (selecting a phenotypic property conferred by the new plasmid), followed by re-isolation of single colonies after growth in the absence of selection for the resident plasmid, and then screening for loss of the resident plasmid (which occurs rapidly due to plasmid incompatability). The resident plasmids routinely used are pRS4(Amp$^r$) or pRS1(ily$^+$, colicin immune). Use of the appropriate resident plasmid allows selection for transformation with virtually every commonly used plasmid that contains a selectable marker, which can then be followed by screening for loss of the resident plasmid. In practice, segregation of the resident plasmid usually occurs so rapidly after introduction of another plasmid that strains with the tRNA$^{trp}$-Su7X mutation can be used to screen for new plasmids that express tRNA$^{trp}$. For example, pLB5 was constructed by cloning the Hpa1-Bgl11 fragments from pRS1 into PvuII-BamH1 cut pBR322. Aftr ligation, the DNA mixture was transformed into strain EM315, selecting ampicillin resistance on LB plates. After colony formation, the colonies were transfered with a flat-ended applicator stick to minimal ampicillin media with and ampicillin media with and without isoleucine and valine. Colonies that contained pLB5 were distinguished because of the prolonged time needed for visible growth on medium with ampicillin but without isoleucine and valine (due to the displacement of pRS1 and its ilv genes from the majority of cells).

EXAMPLE 2

Figure 1:
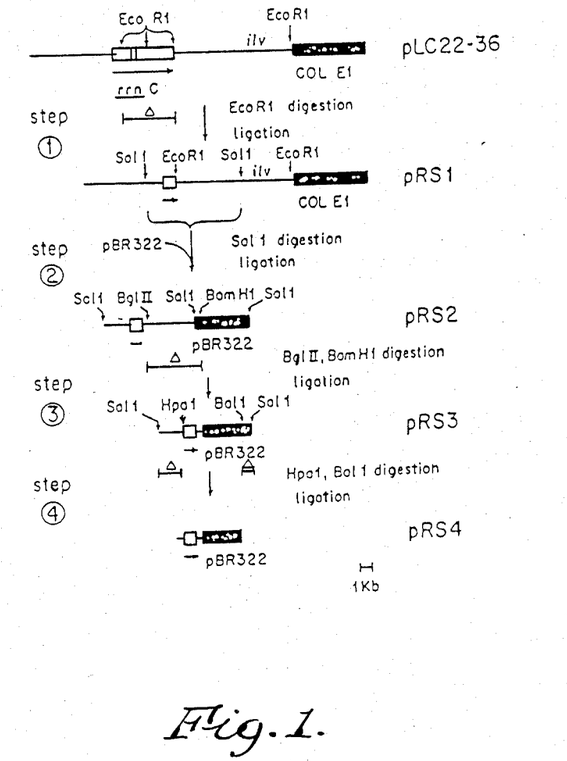

Internal DNA was removed from the complete rrnC operon on the large pLC22-36 plasmid containing a rrnC ribosomal RNA promoter and ribosomal RNA termination sequence by restriction with EcoR1 restriction enzyme. The obtaining of pLC22-36 plasmid is discussed by Morgan et al "Some RNA Operons In *E. coli* Have tRNA Genes At Their Distal ends," Cell, vol. 13, pp. 335–344. This deleted restriction nuclease sites that would hinder subsequent replication (cloning) and demonstrated the viability of bacterial strains harboring a modified rrnC operon. (Step 1 in FIG. 1). The resulting plasmid, pRS1, has a deletion of rrn DNA extending from the middle of the 16S rRNA gene to seven nucleotides before the tRNA$^{asp}$ gene. The tRNA$^{trp}$ gene is eight base pairs (bp) downstream of the tRNA$^{asp}$ gene and is immediately followed by sequences that participate in the base-paired stem of the transcription termination sequence. A Sall fragment of pRS1 was then cloned onto pBR322 plasmid to obtain pRS2 plasmid (FIG. 1). More DNA was removed downstream of the rrnC operon (Step 3 of FIG. 1) to obtain plasmid pRS3. pRS3 was cut with Ball and Hpal and ligated. All resulting plasmids that could be recovered after transformation of bacterial strain EM322 unexpectedly contained less DNA than predicted from circularization of the plasmid at the Ball and Hpal ends. The plasmid with the least DNA deleted, pRS4 (FIG. 2), was analysed extensively by restriction nuclease digestion (data not shown), which revealed that the unexpected deletion in pRS4 included only *E. coli* chromosomal DNA upstream of the BclI site in rrnC. To further define the extent of the deletion the Hpa1-EcoR1 fragment from pRS1 containing the rrnC promoters was labeled with $^{32}P_i$ at the EcoR1 end and annealed to pRS4. A 975 base single stranded fragment was protected from S1 nuclease digestion in this hybrid, demonstrating that the deletion terminates in or near the rrnC P$_1$ promoter, but leaves the rrn P$_2$ promoter and downstream DNA sequences intact. This plasmid is important because it expresses very strongly from a single rrn promoter and may be useful in studies of regulation of rrnC promoters.

Certain plasmids containing both the P$_1$ and the P$_2$ rrnC ribosomal RNA promoters were unstable or lethal when the plasmids are too small; however, it was discovered that the Hpa1-Bgl1II fragment containing the rrnC region of pRS1 could be cloned into PvuII-BamH1 cut pBR322 when we used selections for tRNA$^{trp}$ or nonsense suppressor genes of tRNA$^{trp}$, and the resulting plasmids, pLB5, pLB5-Su7, pLB5-Su8 (FIG. 3), did not undergo problematical rearrangements during routine manipulations. This was surprising, as a DNA sequence between the Ball and PvuII sites of pBR322 codes for a portion of a protein needed to repress copy number. This region was retained during construction of pRS4 but removed during construction of pLB5. Therefore, the rrnC region is stable on pLB5 even though pLB5 probably has a higher copy number than pRS4. The region in which the Hpa1-Bgl1II fragment is inserted may contribute to plasmid instability of lethality, and that the rrn region itself does not invariably lead to plasmid instability of lethality.

pRS4 (FIG. 2) has approximately 180 base pairs of leader DNA between the P$_2$ promoter and the start of the 16S rRNA gene. It was desirable to retain this DNA because of possible involvement in regulation. Most of the remaining 680 base pairs of the 16S rRNA gene were removed by digestion of pRS4 with BclI and XmaI (an isoschizomer of SmaI), followed by filling in the protruding ends with Klenow fragment of DNA polymerase 1 and blunt end ligation to regenerate a SmaI site, giving rise to pRS5 (FIG. 2). pRS5 has 20 base pairs of DNA from near the 5' end of the 16S rRNA gene and 66 base pairs of DNA from near the middle of the 16S rRNA gene. This deletion therefore moves certain restriction nuclease sites nearer to the rrn promoter, reduces the size of the transcript to near the minimum needed to retain all desired features of the rrn operon, and does not interfere with the useful properties of the rrnC tRNA genes. Similar deletions could be introduced into the other plasmids described herein.

Plasmids pRS1, pRS2, pRS3, pRS4, pRS4-Su7, pRS5, pRS5-Su7, pRS5-Su8, pLB5, pLB5-Su7 and pLB5-Su8 are all plasmids in accordance with the present invention which contain a ribosomal RNA rrnC tRNA gene, ribosomal RNA rrnC promoter and rrnC promoter termination sequence with read through sequence.

pRS1 has a total size of about 23,000 base pairs and a ribosomal RNA operon of about 1,300 base pairs. pRS2 has a total size of about 11,300 base pairs and a ribosomal RNA operon of about 1,300 base pairs, pRS3 has a total size of about 7,200 base pairs and a ribosomal RNA operon of about 1,300 base pairs. pRS4 has a total size of about 4,700 base pairs and a ribosomal RNA operon of about 1,300 base pairs. pRS5 has a total size of about 4,100 base pairs and a ribosomal RNA operon of about 700 base pairs. pLB=has a total size of about 4,600 base pairs and a ribosomal RNA operon of about 1300 base pairs. By comparison, starting plasmid pLC22-36 has an overall size of about 27,000 base pairs with a ribosomal RNA operon of about 5,800 base pairs.

Figure 2:
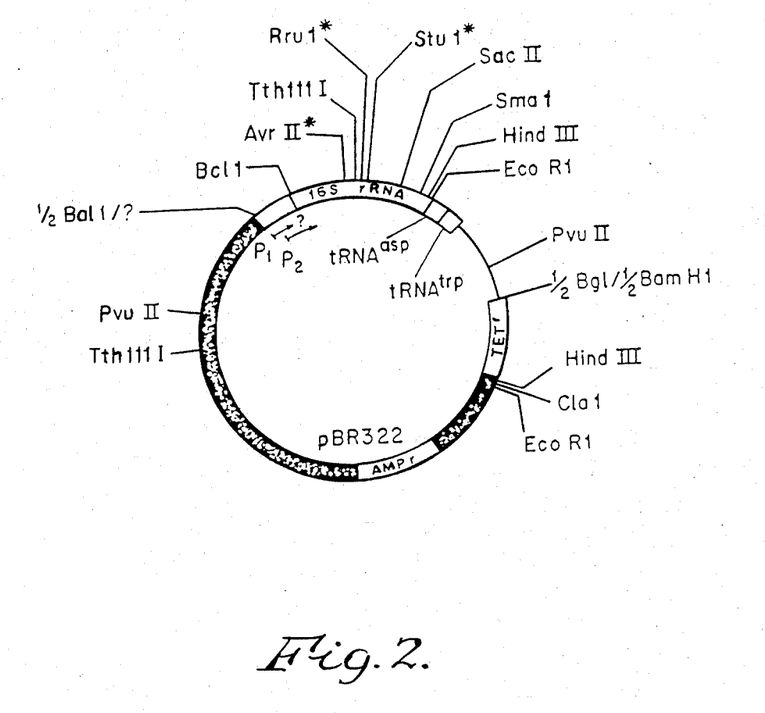
Figure 3:
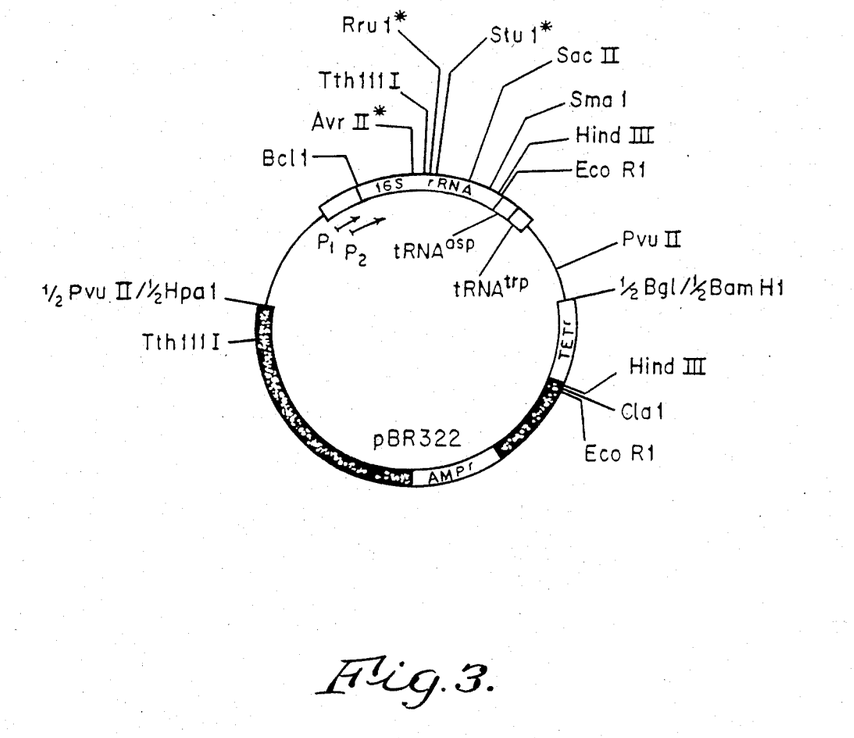

Restriction nuclease sites for the pRS4, pRS5, pRS4-Su7, pRS5-Su7, and the pRS5-Su8 plasmids are as shown in FIG. 2 and for the pLB5, pLB5-Su7, and pLB5-Su8 plasmids are as shown in FIG. 3. Restriction nuclease sites marked with an asterisk are predicted from the sequences of rrnB, rrnC and pBR322, but have not been tested experimentally. All other restriction nuclease sites have been experimentally confirmed. rrn DNA is represented by the white enclosed area and non-rrn chromosomal DNA by the thin line. pRS1, pRS2, pRS3, pRS4, pRS5, and pLB5 plasmid designations as used herein and in the claims are intended to include the Su7 and Su8 derivatives as well as those other modifications which can be easily derived by those skilled in the art.

The plasmids set forth in this example and bacteria, having the defective tRNA$^{trp}$-Su7X chromosomal gene, containing them are available from the State University of New York at Buffalo, Amherst Campus and have been deposited with Northern Regional Research Laboratories, Peoria, Ill. prior to application for this patent. E.coli bacteria having the defective tRNA$^{trp}$-Su7X gene on the chromsome and containing pLC22-36, pRS1, pRS2, pRS3 pRS4, pRS5, and pLB5 plasmids have Northern Regional Research Laboratories deposit numbers NRRLB-15281, NRRLB-15282, NRRLB-15287, NRRLB-15285, NRRLB-15283, NRRLB-15284 and NRRLB-15286, respectively.

EXAMPLE 3

Figure 4:
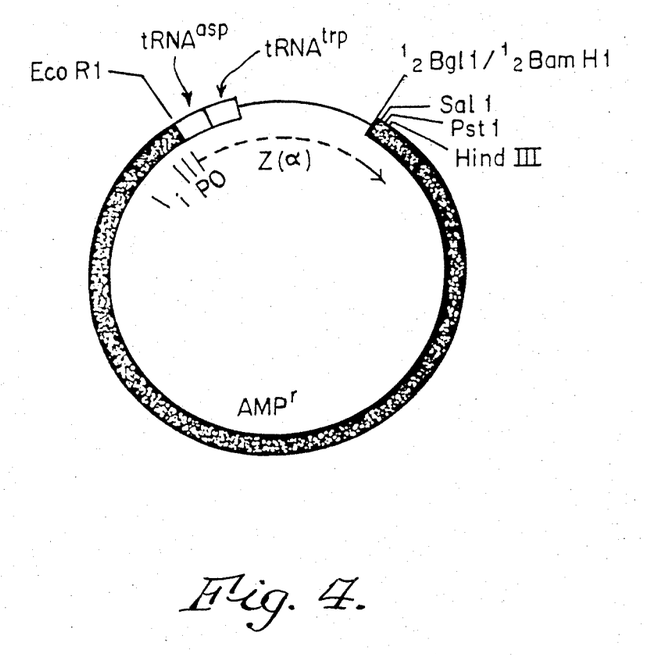

Plasmids were constructed that contain the ribosomal RNA rrnC tRNAs but not the rrnc promoters. This was accomplished by cloning the EcoR1-BglII fragment of pRS1 into EcoR1-BamH1 cut pUC8 (FIG. 4). pUC8 is described by Vieira et al "pUC plasmids, an M13mp7-derived system for insertion mutagenesis and sequencing with synthetic universal primers", Gene, Vol 19, pp. 259-268, 1982. Similar plasmids containing the Su7 and Su8 nonsense suppressing genes of tRNA$^{trp}$ were also constructed.

In these plasmids the tRNA genes are under the control of the lac promoter and an EcoR1 site is provided between the tRNA genes and the lac promoter to allow cloning of other promoters. These plasmids are useful for extending the advantages of the rrnC tRNA genes to other promoters and allow measurement of the strength of rrn promoters relative to other promoters by measuring tRNA over production or the degree of suppression of nonsense mutations in bacterial operons. It is understood that whenever rrn is used herein it refers to a ribosomal RNA operon.

The plasmids of this example are plasmids in accordance with the present invention and have designations pLB6, pLB6-Su7, and pLB6-Su8. These plasmids and bacteria having the defective chromosomal tRNA$^{trp}$-Su7X gene, containing the plasmids are available from The State University of New York at Buffalo, Amherst Campus and plasmid pLB6 has been deposited with Northern Regional Research Laboratories, Peoria, Ill. prior to application for this patent. E.coli bacteria having the defective tRNA$^{trp}$-Su7X gene on the chromosome and containing pLB6 plasmid has Northern Regional Research Laboratories deposit number NRRLB-15288. The Su7 and the Su8 derivatives can be readily made by those skilled in the art. Table 2 shows the characteristics of the deposited plasmids and bacteria containing them.

EXAMPLE 4

A stepwise deletion previously described (especially in Example 2) above allows the monitoring of the effect that each deletion has on tRNA maturation and on the frequency of initiation of RNA polimerage at the rrnC promoters. Expression of the rrnC tRNAs on these plasmids could be measured because the small RNAs coded by the plasmids are over produced in cells carrying the plasmids, and the extent of over production can be determined by 2-dimensional gel electrophoresis of RNAs extracted from growing cells. The methods of electrophoresis for measuring the tRNAs (especially tRNA$^{trp}$) in accordance with the present invention as a means for determining gene expression is the tRNA measurement method set forth by Ikemura et al "Expression of Spacer tRNA Genes in Ribosomol RNA Transcription Units Carried by Hybrid ColE1 plasmids in E. coli," Cell Vol 11, pp. 779-793, 1977. This reference does not however describe or suggest any use of tRNA measurement for determining gene expression in small plasmids within a ribosomal RNA operon. in the methods, cells containing plasmids are labeled with $^{32}P$ for a fixed period of time during steady state growth. The RNA is then extracted and analyzed by electrophoresis through 3% agarose-acrylomide composite gels.

TABLE 1

| Bacterial Strain | Description |
| --- | --- |
| EM4 | F$^+$ ilv1 his29(amber) pro2 tsx$^r$ trpA9605 (amber) trpR55 |
| EM22 | ara(amber) galK(amber) galE lac(amber) tsx$^r$ ilv recA |
| EM315 | pRS1/ara(amber) galK(amber) galE lac(amber) trp(amber) tsx$^r$ ilv recA $^{\lambda r}$ Str$^r$ trpT-Su7X |
| EM317 | pRS4/ara(amber) galK(amber) galE lac(amber) trp(amber) tsx$^r$ ilv recA $^{\lambda r}$ Str$^r$ trpT-Su7X |
| EM322 | ara(amber) galK(amber) galE lac(amber) trp(amber) tsx$^r$ ilv recA $^{\lambda r}$ Str$^r$ |
| EM323 | pRS5/ara(amber) galK(amber) galE lac(amber) trp(amber) tsx$^r$ ilv recA $^{\lambda r}$ Str$^r$ trpT-Su7X |
| EM324 | pLC22-36/ara(amber) galK(amber) galE lac(amber) trp(amber) tsx$^r$ ilv recA $^{\lambda r}$ Str$^r$ trpT-Su7X |
| EM340 | pLB5/ara(amber) galK(amber) galE lac(amber) trp(amber) tsx$^r$ ilv recA $^{\lambda r}$ Str$^r$ TrpT-Su7X |

TABLE 2

| Strain | Designation | Genotype | Deposit # |
| --- | --- | --- | --- |
| 1. | pLC22-36/ EM22 | pLC22-36/ara(amber) galK(amber) galE lac(amber) trp(amber) tsx$^r$ ivl recA | NRRLB-15281 |
| 2. | EM315 | pRS1/ara(amber) galK(amber) galE lac(amber) trp(amber) tsx$^r$ ilv recA $^{\lambda r}$ Str$^r$ trpT-Su7X | NRRLB-15282 |
| 3. | EM314 | pRS4/ara(amber) galK(amber) galE lac(amber) trp(amber) tsx$^r$ ilv recA $^{\lambda r}$ Str$^r$ trpT-Su7X | NRRLB-15283 |
| 4. | EM323 | pRS5/ara(amber) galK(amber) galE lac(amber) trp(amber) tsx$^r$ ilv recA $^{\lambda r}$ Str$^r$ trpT-Su7X | NRRLB-15284 |

TABLE 2-continued

| Strain | Designation | Genotype | Deposit # |
|---|---|---|---|
| 5. | EM329 | pRS3/ara(amber) galK(amber) galE lac(amber) trp(amber) tsx$^r$ ilv recA $^{\lambda r}$ Str$^r$ trpT-Su7X | NRRLB-15285 |
| 6. | EM340 | pLB5/ara(amber) galK(amber) galE lac(amber) trp(amber) tsx$^r$ ilv recA $^{\lambda r}$ Str$^r$ trpT-Su7X | NRRLB-15286 |
| 7. | pRS2/EM2 | pRS2/F$^+$ilvl his29(amber) pro2 tsx$^r$ trpR55 trpA9605(amber) | NRRLB-15287 |
| 8. | pLB6/EM322 | pLB6/ara(amber) galK(amber) galE lac(amber) trp(amber) tsx$^r$ ilv recA $^{\lambda r}$ Str$^r$ | NRRLB-15288 |

What is claimed is:

1. A bacterium comprising chromosomal DNA which lacks a DNA sequence which effectively codes for a functional tRNA for tryptophan and further comprising a plasmid which has a DNA sequence which does effectively code for said tRNA for tryptophan.

2. The bacterium of claim 1 wherein the bacterium is an *E. coli*.

3. The bacterium of claim 1 wherein the DNA sequence for said tRNA for tryptophan is located between a rrn A-H or a homologous functionally equivalent rRNA promoter and a ribosomal RNA promoter termination sequence within said plasmid.

4. The bacterium of claim 3 wherein the bacterium is an *E. coli*.

* * * * *